US00PP16950P2

(12) United States Plant Patent
Bunker

(10) Patent No.: US PP16,950 P2
(45) Date of Patent: Aug. 8, 2006

(54) ***BRACTEANTHA* PLANT NAMED 'FLOBRAFLA'**

(50) Latin Name: *Bracteantha bracteata*
Varietal Denomination: Flobrafla

(75) Inventor: Kerry Veianne Bunker, Redland Bay (AU)

(73) Assignee: Floreta Pty. Ltd., Redland (AU); Trustee for the Sundaze Beauty Trust ( * ) Notice: Subject to any disclaimer, the term of this patent is extended or adjusted under 35 U.S.C. 154(b) by 0 days.

(21) Appl. No.: 11/108,575

(22) Filed: Apr. 15, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Bracteantha* named 'Flobrafla', characterized by its compact and bushy growth habit; upright and rounded plant form; freely-flowering habit; bronzed orange and golden yellow bi-colored involucral bracts and golden yellow-colored disc florets; and short and strong peduncles that hold inflorescences above the foliage.

1 Drawing Sheet

Botanical designation: *Bracteantha bracteata.*
Cultivar denomination: 'Flobrafla'.

BACKGROUND OF THE INVENTION

The present invention relates to a new and distinct cultivar of *Bracteantha* plant, botanically known as *Bracteantha bracteata* and referred to by the name 'Flobrafla'.

The new *Bracteantha* is a product of a planned breeding program conducted by the Inventor in Redland Bay, Queensland, Australia. The objective of the program is to create and develop new compact *Bracteantha* cultivars with numerous inflorescences, attractive involucral bract coloration and long-lasting inflorescences.

The new *Bracteantha* originated from a cross-pollination by the Inventor in January, 1999, of a proprietary selection of *Bracteantha bracteata* identified as code number 97-004, not patented, as the female, or seed, parent with an unknown selection of *Bracteantha bracteata,* as the male, or pollen, parent. The new *Bracteantha* was discovered and selected by the Inventor as a plant within the progeny of the stated cross-pollination in a controlled environment in Redland Bay, Queensland, Australia in September, 2000.

Asexual reproduction of the new *Bracteantha* by terminal cuttings in a controlled environment in Redland Bay, Queensland, Australia since May, 2001, has shown that the unique features of this new *Bracteantha* are stable and reproduced true to type in successive generations.

SUMMARY OF THE INVENTION

The new *Bracteantha* has not been observed under all possible environmental conditions. The phenotype may vary somewhat with variations in environment such as temperature and light intensity without, however, any variance in genotype.

The following characteristics have been repeatedly observed and are determined to be basic characteristics of 'Flobrafla' and distinguish the new *Bracteantha* as a new and distinct cultivar:

1. Compact and bushy growth habit.
2. Upright and rounded plant form.
3. Freely-flowering habit.
4. Bronzed orange and golden yellow bi-colored involucral bracts and golden yellow-colored disc florets.
5. Short and strong peduncles that hold inflorescences above the foliage.

Plants of the new *Bracteantha* can be compared to plants of the female parent selection. In side-by-side comparisons conducted by the Inventor in Redland Bay, Queensland, Australia, plants of the new *Bracteantha* differed from plants of the female parent selection in the following characteristics:

1. Plants of the new *Bracteantha* were more compact and denser than plants of the female parent selection.
2. Plants of the new *Bracteantha* and the female parent selection differed in involucral bract coloration as plants of the female plant had orange-colored involucral bracts.

Plants of the new *Bracteantha* can also be compared to plants of the cultivar Redbragol, disclosed in U.S. Plant Pat. No. 12,988. In side-by-side comparisons conducted by the Inventor in Redland Bay, Queensland, Australia, plants of the new *Bracteantha* differed from plants of the cultivar Redbragol in the following characteristics:

1. Inflorescences of plants of the new *Bracteantha* were flat and not as cupped as inflorescences of plants of the cultivar Redbragol.
2. Plants of the new *Bracteantha* were more freely flowering than plants of the cultivar Redbragol.
3. Inflorescences of plants of the new *Bracteantha* had fewer involucral bracts and disc florets than inflorescences of plants of the cultivar Redbragol.
4. Plants of the new *Bracteantha* and the cultivar Redbragol differed in involucral bract coloration as plants of the cultivar Redbragol had yellow-colored involucral bracts.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Bracteantha*.

The photograph at the top of the sheet comprises a side perspective view of a typical plant of 'Flobrafla' grown in a container.

The photograph at the bottom of the sheet is a close-up view of a typical inflorescence of 'Flobrafla'. Plants used in the photographs were grown in 14-cm containers and were about three months old.

DETAILED BOTANICAL DESCRIPTION

The following observations and measurements describe plants grown in Redland Bay, Queensland, Australia during the spring and summer under full sun outdoor conditions, day temperatures ranging from 22 to 35° C. and night temperatures ranging from 15 to 20° C. Rooted liners of the new *Bracteantha* were planted in 250-mm containers and grown for about six months. Color references are made to The Royal Horticultural Society Colour Chart, 1995 Edition, except where general terms of ordinary dictionary significance are used.

Botanical classification: *Bracteantha bracteata* cultivar Flobrafla.

Parentage:

*Female or seed parent.*—Proprietary selection of *Bracteantha bracteata* identified as code number 97-004, not patented.

*Male or pollen parent.*—Unknown selection of *Bracteantha bracteata.*

Propagation:

*Type.*—By cuttings.

*Time to initiate roots.*—Summer: About one week at 30° C. Winter: About two weeks at 20° C.

*Time to produce a rooted young plant.*—Summer: About three weeks at 30° C. Winter: About four weeks at 20° C.

*Root description.*—Fine to fibrous; pale brown in color.

*Rooting habit.*—Freely-branching.

Plant description:

*General appearance.*—Compact and bushy growth habit; upright and rounded plant form with dense foliage and inflorescences held above the foliage on short peduncles. Vigorous growth habit. Freely branching, about 202 lateral branches per plant.

*Plant height.*—About 25 cm.

*Plant width.*—About 45 cm.

*Lateral branch description.*—Length: About 24 cm. Width: About 5 mm. Internode length: About 8 mm. Aspect: Erect. Strong: Strong. Texture: Slightly pubescent. Color: 147C.

*Foliage description.*—Arrangement: Alternate, single; sessile. Length: About 6.1 cm. Width: About 1.1 cm. Shape: Linear elliptic. Apex: Acute. Base: Attenuate. Margin: Entire. Texture, upper and lower surfaces: Smooth, glabrous. Venation pattern: Pinnate. Color: Developing leaves, upper surface: 137B. Developing leaves, lower surface: 137C. Fully expanded leaves, upper surface: 137A; venation, 137A. Fully expanded leaves, lower surface: 137C; venation, 147C.

Flowering description:

*Inflorescence form.*—Daisy-type composite inflorescence form. Involucral bracts and disc florets develop arranged acropetally on a capitulum. Inflorescences circular in shape; flattened.

*Inflorescence longevity.*—Inflorescences last on the plant for about 36 days. Inflorescences persistent.

*Natural flowering season.*—Natural flowering season is year-round in Redland Bay, Queensland, Australia; flowering continuous.

*Quantity of inflorescences.*—One terminal inflorescence per lateral branch, about 192 open inflorescences and inflorescence buds per plant.

*Fragrance.*—Moderate; sweet.

*Inflorescence diameter.*—About 3.5 cm.

*Inflorescence depth (height).*—About 1.1 cm.

*Disc diameter.*—About 1 cm.

*Receptacle diameter.*—About 1 cm.

*Receptacle height.*—About 1.2 mm.

*Inflorescence buds.*—Length: About 1.5 cm. Diameter: About 1.6 cm. Shape: Roughly ovoid. Color: Mostly 167B; towards the apex, 166A; mid-section, 172B.

*Involucral bracts.*—Quantity per inflorescence: About 90 in multiple whorls. Length: About 1.2 cm. Width: About 5.5 mm. Shape: Ligulate, concave. Apex: Acute. Base: Truncate. Margin: Entire. Texture, upper and lower surfaces: Smooth, papery, stiff. Color: Inner whorls, upper surface: 7B. Center whorls, upper surface: 17A. Outer whorls, upper surface: Towards the apex, 178B to 172C; towards the base, 17A. Inner whorls, lower surface: 7B. Center whorls, lower surface: 17B. Outer whorls, lower surface: 172B.

*Disc florets.*—Arrangement: Massed in the center of the receptacle with one whorl of filiform florets at the perimeter of the disc. Quantity per inflorescence: About 363. Shape: Tubular with five lobes. Length: About 8.5 mm. Diameter, apex: About 0.8 mm. Diameter, base: About 0.7 mm. Color, immature and mature: 23B.

*Peduncle.*—Length: About 2 cm. Diameter: About 2 mm. Aspect: Erect. Strength: Strong. Texture: Slightly pubescent. Color: 147C.

*Androecium.*—Present only on disc florets; minute. Arrangement: Fused anther tube with five long thin linear anthers surrounding the style. Anther length: Less than 1 mm. Anther color: Yellow. Amount of pollen: Moderate. Pollen color: Yellow.

*Gynoecium.*—Present on both filiform and disc florets; minute. Quantity per floret: One. Style color: 23A. Stigma shape: Bi-parted. Stigma color: 23A.

*Seed.*—Length: About 2.4 mm. Diameter: About 0.9 mm. Color: 200C.

Disease/pest resistance: Plants of the new *Bracteantha* have not been observed to be resistant to pathogens or pests common to *Bracteantha.*

Temperature tolerance: Plants of the new *Bracteantha* have been observed to tolerate temperatures from −4 to 40° C.

It is claimed:

1. A new and distinct cultivar of *Bracteantha* plant named 'Flobrafla', as illustrated and described.

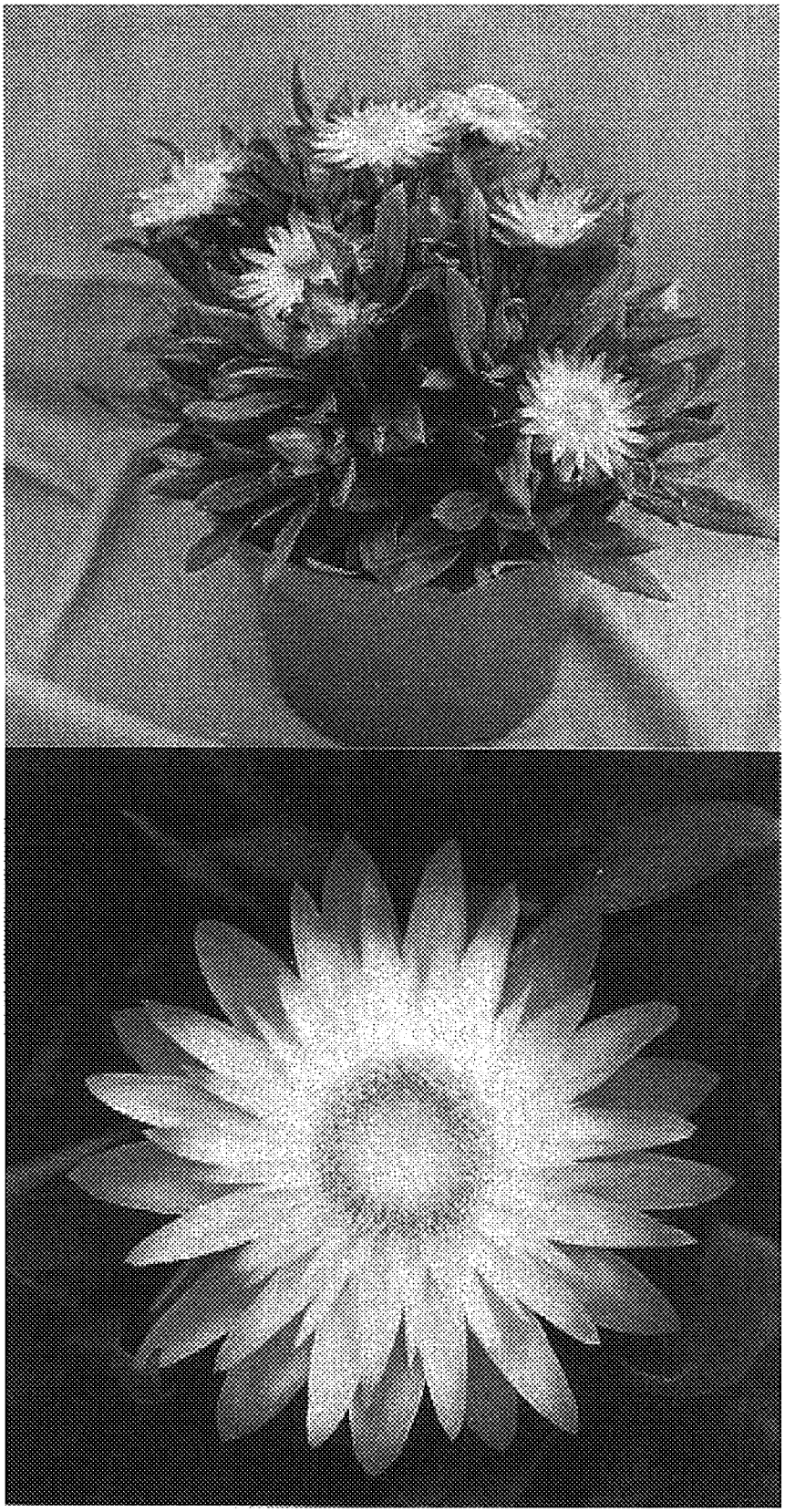

* * * * *